(12) United States Patent
Rasolzadeh et al.

(10) Patent No.: US 12,400,437 B2
(45) Date of Patent: Aug. 26, 2025

(54) MODEL COMBINING AND INTERACTION FOR MEDICAL IMAGING

(71) Applicant: Arterys Inc., San Francisco, CA (US)

(72) Inventors: Babak Rasolzadeh, San Francisco, CA (US); Maya Khalife, San Francisco, CA (US); Christian Arne Ulstrup, Milton, DE (US)

(73) Assignee: Arterys Inc., San Francisco, CA (US)

( * ) Notice: Subject to any disclaimer, the term of this patent is extended or adjusted under 35 U.S.C. 154(b) by 601 days.

(21) Appl. No.: 17/741,384

(22) Filed: May 10, 2022

(65) Prior Publication Data

US 2022/0366680 A1    Nov. 17, 2022

Related U.S. Application Data

(60) Provisional application No. 63/187,676, filed on May 12, 2021.

(51) Int. Cl.
*G06V 10/80* (2022.01)
*G06T 11/00* (2006.01)
*G06V 10/70* (2022.01)
*G16H 30/40* (2018.01)

(52) U.S. Cl.
CPC .............. *G06V 10/80* (2022.01); *G06T 11/00* (2013.01); *G06V 10/87* (2022.01); *G16H 30/40* (2018.01); *G06T 2210/41* (2013.01)

(58) Field of Classification Search
CPC ........ G06V 10/80; G06V 10/87; G16H 30/40; G06T 11/00; G06T 2210/41
USPC ......................................................... 382/128
See application file for complete search history.

(56) References Cited

U.S. PATENT DOCUMENTS

| 2014/0176602 | A1* | 6/2014 | Yoshihara | ............. | G06T 7/0014 |
| | | | | | 345/629 |
| 2021/0005307 | A1* | 1/2021 | Knoplioch | ............. | G16H 10/60 |
| 2021/0081720 | A1 | 3/2021 | Polleri et al. | | |

OTHER PUBLICATIONS

International Search Report and Written Opinion, mailed Jul. 26, 2022, for International Application No. PCT/US2022/028573, 16 pages.

* cited by examiner

*Primary Examiner* — Michael R Neff
(74) *Attorney, Agent, or Firm* — Seed Intellectual Property Law Group LLP

(57) ABSTRACT

This disclosure relates to the combining and interaction of multiple artificial intelligence (AI) models for medical image analysis. An example method includes obtaining AI models from model providers and organizing them to form associations. In response to a user request, base models are selected and provided. Additional models are further selected to combine with the base models, and medical image analysis results are presented based on applying a combination of the models to target medical image data.

20 Claims, 13 Drawing Sheets
(9 of 13 Drawing Sheet(s) Filed in Color)

MODEL COMBINING AND INTERACTION FOR MEDICAL IMAGING

CROSS-REFERENCE TO RELATED APPLICATIONS

This application claims the benefit of priority to U.S. Provisional Application No. 63/187,676, filed May 12, 2021, which application is hereby incorporated by reference in its entirety.

BACKGROUND

Technical Field

This disclosure relates generally to medical imaging applications, and, more particularly, to the combining and interaction of multiple artificial intelligence (AI) models for medical image analysis.

Description of the Related Art

Medical images usually consist of two-dimensional images, three-dimensional images, or reconstructed fused images generated through imaging equipment utilizing modern nuclear medicine techniques, for example, positron emission tomography (PET), computed tomography (CT), magnetic resonance imaging (MRI), functional MM (fMRI), X-ray, mammography, tomosynthesis, ultrasound or other modalities. Medical images may be viewed by the patient or health professionals in the course of rendering diagnosis, treatment, or other health care.

AI models can be used to facilitate the analysis of medical images. For example, a model in machine learning is the output of a machine learning algorithm run on data. The model is typically saved after running a machine learning algorithm on training data (e.g., medical images that were collected in the past) and represents the rules, numbers, and any other algorithm-specific data structures required to make predictions. Illustratively, a linear regression algorithm results in a model comprised of a vector of coefficients with specific values, a decision tree algorithm results in a model comprised of a tree of if-then statements with specific values, and neural network backpropagation or gradient descent algorithms can result in a model comprised of a graph structure with vectors or matrices of weights with specific values.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The embodiments of this disclosure are illustrated by way of example and not limitation in the figures of the accompanying drawings, in which like references indicate similar elements and in which.

Figure 1:
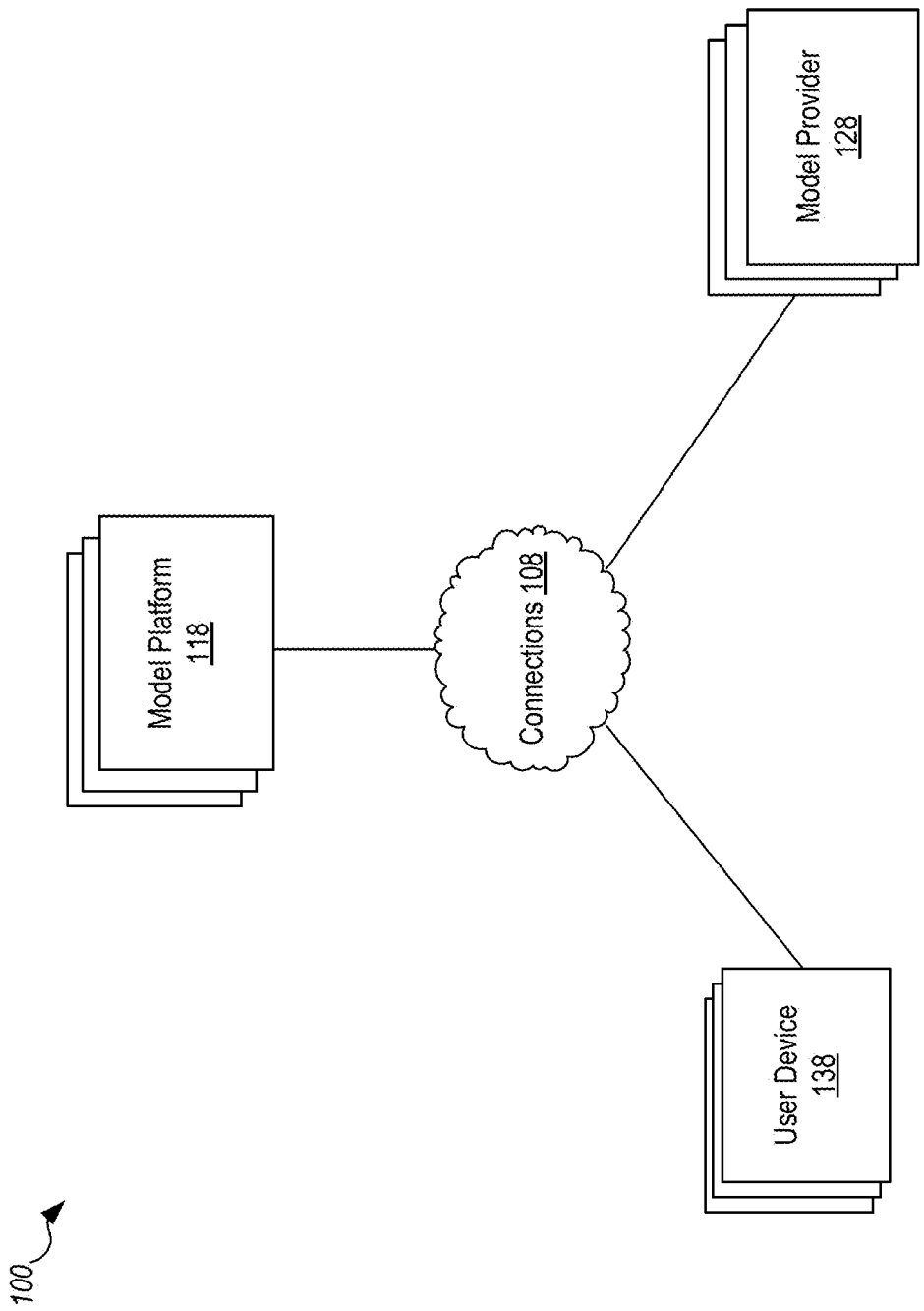
FIG. 1 is a block diagram illustrating an example networked environment for one or more model platforms in accordance with at least some embodiments of the techniques described herein.

Other features of the present embodiments will be apparent from the accompanying drawings and from the detailed description that follows.

DETAILED DESCRIPTION

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks and the environment, have not been shown or described in order to avoid unnecessarily obscuring descriptions of the embodiments. Additionally, the various embodiments may be methods, systems, media, or devices. Accordingly, the various embodiments may combine software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

References to the term "set" (e.g., "a set of items"), as used herein, unless otherwise noted or contradicted by context, is to be construed as a nonempty collection comprising one or more members or instances.

References to the term "subset" (e.g., "a subset of the set of items"), as used herein, unless otherwise noted or contradicted by context, is to be construed as a nonempty collection comprising one or more members or instances of a set or plurality of members or instances.

Moreover, the term "subset," as used herein, refers to a proper subset, which is a collection of one or more members or instances that are collectively smaller in number than the set or plurality of which the subset is drawn. For instance, a subset of a set of ten items will have less than ten items and at least one item.

Various applications, methods and systems are disclosed herein to provide improved communication, integration, utilization, and collaboration for AI based medical imaging environments. The described embodiments provide a digital platform that enables various combinations and interactions of AI models, to achieve innovative and effective medical imaging analysis that is far more than the sum of individual AI model outcomes. For example, the platform facilitates combining complementary models to generate AI-enhanced layer(s) over image data, combining models of the same or similar type to produce and present "average" or otherwise enhanced results, and generating and processing configurable workflows where models can be chained or otherwise linked into a logical flow. Further, the platform generates various novel user interfaces or instructions for such interfaces to be presented remotely (e.g., on user devices). With these user interfaces, a user can control, guide, or otherwise interact with unified AI model processing and outcome presentation.

In some embodiments, the user interfaces include a panel view, which enables combinations of complementary models (e.g., models that are designed to generate different types of analysis results) to generate an AI-enhanced layer atop or beside image data. For example, the user interface can present bounding boxes for object detection and localization, graded heat maps corresponding to clinical metrics, or other image overlay enhancements that are generated based on the complementary model results. Additionally, clinically relevant metrics and statistics (e.g. likelihood of lesion malignancy and an accompanying confidence score) can be presented on the side of the medical image. The user can toggle these overlay enhancements and analyses on or off.

In some embodiments, the user interfaces include a harmonized view, which enables combinations of models of the same or similar type (e.g., models that provide different values for the same or overlapping parameters) to produce enhanced outputs (e.g., by using averages, intersections, unions, or the like). For example, given a chest CT image, three lesion detection models can be combined to create slice-level annotation masks visible only in the regions of an image where there is concordance between all three, and the odds of there being a malignant lesion requiring medical intervention can be a weighted average percent from all three models.

In some embodiments, the user interfaces include a workflow view which enables individual models to be linked together to feed one or more models' outputs to other models as inputs. Illustratively, a user can, within the same view of the image, search for additional models to apply to the image. The search can be done with text input, by viewing popular models, or with other automatically applied filters that take into account the type of image(s) being viewed. Once the user selects additional models, the user interface enables the user to "pull" them into the workflow, which can be a chain, a tree, a lattice, or other hierarchies to collectively produce and render medical imaging analysis results based on the current images.

In some embodiments, the various configurations for combining models and generating their corresponding user interfaces can be saved and shared between users. For example, a radiation oncologist may save a three-model "panel" to enhance and make more efficient his brain metastases segmentation workflow. The three models can include two models that volumetrically segment the mets and one model that provides a prognostic score (e.g. probability of patient survival over the next two years). This three-model combination can be shared with colleagues and research collaborators, and applied to medical image series that meet criteria specific to the combination (e.g., as defined by a range of acceptable image header values).

FIG. 1 is a block diagram illustrating an example networked environment 100 for one or more model platforms in accordance with at least some embodiments of the techniques described herein. The exemplary networked environment 100 includes one or more model platforms 118, one or more model providers 128, and one or more user devices 138, which are interconnected with one another via at least some part of connections 108.

In the depicted exemplary networked environment 100, the connections 108 may comprise one or more computer networks, one or more wired or wireless networks, satellite transmission media, one or more cellular networks, or some combination thereof. The connections 108 may include a publicly accessible network of linked networks, possibly operated by various distinct parties, such as the Internet. The connections 108 may include other network types, such as one or more private networks (e.g., corporate or university networks that are wholly or partially inaccessible to non-privileged users), and may include combinations thereof, such that (for example) one or more of the private networks have access to or from one or more of the public networks. Furthermore, the connections 108 may include various types of wired or wireless networks in various situations, including satellite transmission. In addition, the connections 108 may include one or more communication interfaces to individual entities in the networked environment 100, various other mobile devices, computing devices and media devices, including but not limited to, radio frequency (RF) transceivers, cellular communication interfaces and antennas, USB interfaces, ports and connections (e.g., USB Type-A, USB Type-B, USB Type-C (or USB-C), USB mini A, USB mini B, USB micro A, USB micro C), other RF transceivers (e.g., infrared transceivers, Zigbee® network connection interfaces based on the IEEE 802.15.4 specification, Z-Wave® connection interfaces, wireless Ethernet ("Wi-Fi") interfaces, short range wireless (e.g., Bluetooth®) interfaces and the like.

In various embodiments, examples of a user device 138 include, but are not limited to, one or a combination of the following: a "computer," "mobile device," "tablet computer," "smart phone," "handheld computer," or "workstation," etc. The user device(s) 138 may be any suitable computing device or electronic equipment that is, e.g., operable to communicate with the model platform(s) 118, and to interact with user(s) for utilizing AI or other computational models that are contributed by the model provider(s) and hosted on the model platform(s) 118.

In various embodiments, individual model platforms 118 and model providers 128 can be implemented in software or hardware form on one or more computing devices including a "computer," "mobile device," "tablet computer," "smart phone," "handheld computer," or "workstation," etc. The model platform(s) 118 can perform model intake, model hosting, model grouping or association, model training, model execution, candidate model selection, model combining, model performance monitoring and feedback, or other model-related functions described herein. The model provider(s) 128 can provide AI or other computational models (e.g., that are designed or trained by developers) and associated model metadata, as well as processing model performance feedback, or other model-related functions. A model provider 128 can be a user device 138 or a model platform 118 in accordance with at least some implementation of the presently disclosed technology.

Data communications among entities of the networked environment 100 can be encrypted. Related encryption and decryption may be performed as applicable according to one or more of any number of currently available or subsequently developed encryption methods, processes, standards, protocols, or algorithms, including but not limited to: encryption processes utilizing a public-key infrastructure (PKI), encryption processes utilizing digital certificates, the Data Encryption Standard (DES), the Advanced Encryption Standard (AES 128, AES 192, AES 256, etc.), the Common Scrambling Algorithm (CSA), encryption algorithms supporting Transport Layer Security 1.0, 1.1, or 1.2, encryption algorithms supporting the Extended Validation (EV) Certificate, etc.

The above description of the exemplary networked environment 100 and the various service providers, systems, networks, and devices therein is intended as a broad, non-limiting overview of an exemplary environment in which various embodiments of the facility may be implemented. FIG. 1 illustrates just one example of an operating environment, and the various embodiments discussed herein are not limited to such environments. In particular, the networked environment 100 may contain other devices, systems or media not specifically described herein.

Figure 2:
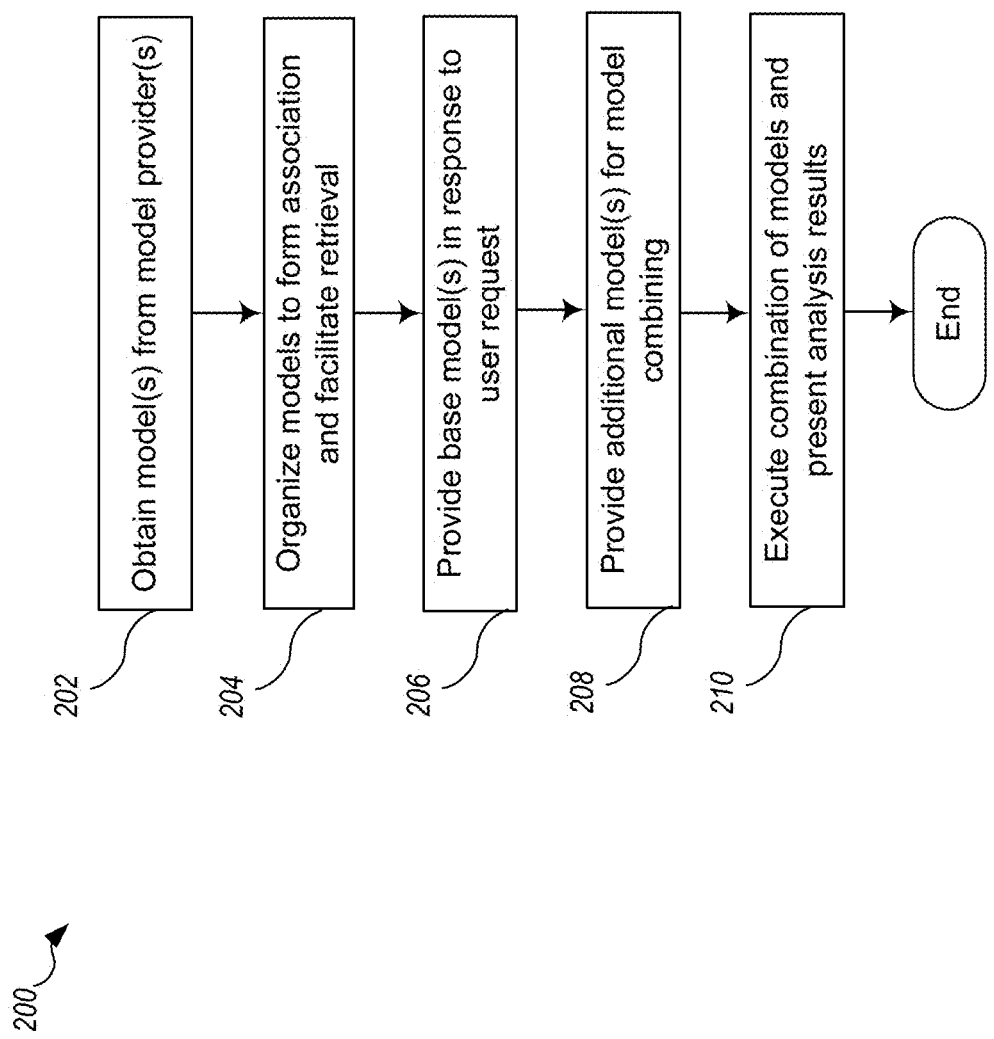
FIG. 2 is a flow diagram illustrating an example process for organizing and combining models in accordance with at least some embodiments of the techniques described herein.

FIG. 2 is a flow diagram illustrating an example process 200 for organizing and combining models in accordance with at least some embodiments of the techniques described herein. Illustratively, the process 200 can be implemented by a model platform 118, and in some instances, in communication with one or more model providers 128 and user devices 138.

At block 202, the process 200 includes obtaining one or more AI or other computational models from the model provider(s) 128. The model platform 118 can implement an interface (e.g., via HTTP, FTP, or other applicable protocols) where model provider(s) 128 can upload models. In some embodiments, training data, testing data, or metadata associated with the model(s) can also be uploaded. The metadata can include descriptions about the input, output, structure, or parameters of the model, for example. The metadata can conform to pre-defined grammar, keywords or textural structure, so that it can be quickly parsed by the model platform 118 in accordance with certain pre-defined rules. In some embodiments, the metadata does not conform to any defined grammar or structure, and can include freeform texts. In these cases, the model platform 118 can implement applicable natural language processing techniques to analyze the content of the metadata. In some embodiments, the model platform 118 can analyze the uploaded model itself and determine its input, output, structure, or parameters, without accessing metadata.

At block 204, the process 200 includes organizing the models (e.g., previously obtained and newly obtained) to form associations among them and thereby facilitate their retrieval. Illustratively, the model platform 118 can organize the models into groups or multiple levels of groups and subgroups. As non-limiting examples, grouping criteria can be the similarity of input or output of models, overlaps between a model's output and another model's input, or structural similarity of models. Individual groups (or subgroups) may or may not include model(s) in common, and may reference one another to provide further flexibility in associating the models with one another.

At block 206, the process 200 includes providing one or more base models in response to a user request. In some embodiments, the user request is generated based on a user's interaction with one or more user interfaces described herein in accordance with the presently disclosed technology. The user request can be transmitted from a user device 138 to the model platform 118. The user request can indicate an analysis purpose, context, applicable medical data, model structure, model input and output, or performance requirement. Based on the user request, the model platform 118 searches the organized models, selects the one or more base models, and provides them to the user device 138 (e.g., via the one or more user interfaces).

At block 208, the process 200 includes providing one or more additional models for model combining. As described above, model combining can include combining complementary models (e.g., to generate AI-enhanced layer(s) over image data), combining models of the same or similar type (e.g., to produce and present enhanced, integrated results), or generating and processing configurable workflow(s) (e.g., so that models can be linked into a logical flow to produce results as a whole).

In some embodiments, complementary models are models designed to receive the same or overlapping input features and to generate different output features (e.g., for different analyses or purposes). In some embodiments, models of the same or similar type are different models designed to generate the same or overlapping output features (e.g., for the same or similar analyses or purposes). Models of the same or similar type may be structurally different, having different values for their internal parameters, or designed to receive different input features. In some embodiments, models that are linkable to form a configurable workflow have compatibility between their inputs and outputs. For example, if model A's output features match model B's input features, then model A can be linked to model B. Further, multiple models' outputs can be combined (e.g., their output features or subsets thereof are selectively concatenated) to match another model's input, a single model's output can be selectively subdivided to match multiple other models' inputs, and multiple models' outputs can be selectively combined or subdivided into different feature combinations to match multiple other model's inputs.

Based on the base model(s) or in response to additional user request(s), the model platform 118 can search the organized models in accordance with the models' associations, and identify candidate models for combining with the base model(s). In some embodiments, the model platform 118 can further generate "dummy," "padding," or other neutral features to supplement certain models' input or output, and thereby facilitating the combining of the models.

At block 210, the process 200 includes executing the combination of models and presenting analysis results. As described above, the model platform 118 can generate various user interfaces or instructions for such interfaces to be presented remotely (e.g., on user devices via a browser or app). With these user interfaces, a user can control, guide, or otherwise interact with unified AI model processing and outcome presentation. For example, the user can select from the candidate models to combine with the base model(s) or previously selected model(s), select medical data for model training, re-training, or testing, customize various views associated with the model combining and result presentation, provide feedback on performance of individual models or model combination(s), save the model combination or user interface settings for sharing with other users.

Figure 3:
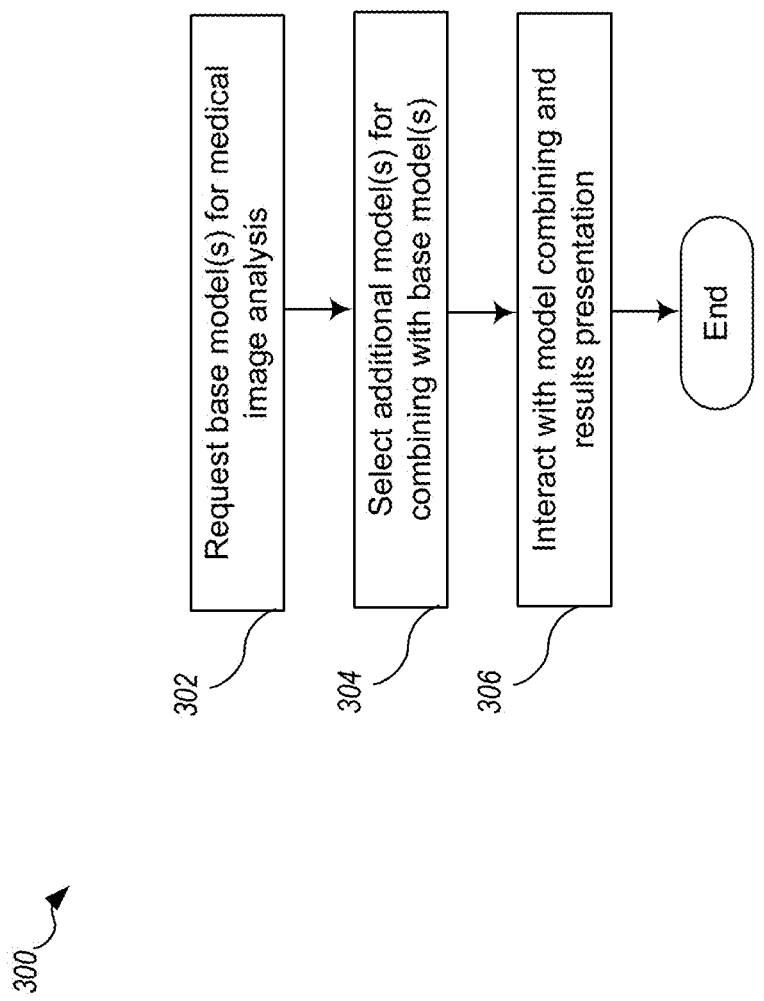
FIG. 3 is a flow diagram illustrating an example process for medical image analysis based on model combining, in accordance with at least some embodiments of the techniques described herein.

FIG. 3 is a flow diagram illustrating an example process 300 for medical image analysis based on model combining, in accordance with at least some embodiments of the techniques described herein. Illustratively, the process 300 can be implemented by a user device 138 in communication with one or more model platforms 118.

At block 302, the process 300 includes requesting one or more base models for medical image analysis. In some embodiments, the user device 138 generates a user request based on a user's interaction with one or more user interfaces described herein in accordance with the presently disclosed technology. The user request can be transmitted from the user device 138 to the model platform 118. In some embodiments, the user request specifies the base model(s). For example, the user selects the base model(s) by browsing through various models organized and searchable via applicable user interfaces, and the user device 138 generates the user request including identifiers corresponding to the selected base model(s). In some embodiments, the user request can indicate an analysis purpose, context, applicable medical data, model structure, model input and output, or performance requirement. Based on the user request, the model platform 118 searches the organized models, selects the one or more base models, and provides them to the user device 138 (e.g., via the one or more user interfaces).

At block 304, the process 300 includes selecting one or more additional models for model combining. As described above, model combining can include combining complementary models (e.g., to generate AI-enhanced layer(s) over image data), combining models of the same or similar type (e.g., to produce and present enhanced, integrated results), or generating and processing configurable workflow(s) (e.g., so that models can be linked into a logical flow to produce results as a whole).

In some embodiments, the user device 138 generates additional user request(s) based on the user's interaction with one or more user interfaces described herein in accordance with the presently disclosed technology. The additional user request(s) can specify the additional model(s) for combining. For example, the user selects the additional model(s) associated with the base model(s) or previously selected model(s), by browsing through various models organized and searchable via applicable user interfaces, and the user device 138 generates the additional user request(s) including identifiers corresponding to the selected additional model(s). In some embodiments, the additional user request(s) can indicate an analysis purpose, context, applicable medical data, model structure, model input and output, or performance requirement for the additional models.

Based on the base model(s) or in response to additional user request(s), the model platform 118 can search the organized models in accordance with their associations, and identify candidate models for combining with the base model(s). In some embodiments, the model platform 118 can further generate "dummy," "padding," or other neutral features to supplement certain model's input or output, and thereby facilitating the combining of the models.

At block 306, the process 300 includes interacting with model combining and analysis results presentation. As described above, the model platform 118 can generate various user interfaces or instructions for such interfaces to be presented remotely (e.g., on user devices). With these user interfaces, a user can control, guide, or otherwise interact with unified AI model processing and outcome presentation. For example, the user can select from the candidate models to combine with the base model(s) or previously selected model(s), select medical data for model training, re-training, or testing, customize various views associated with the model combining and result presentation, provide feedback on performance of individual models or model combination(s), save the model combination or user interface settings for sharing with other users.

Figure 5A:
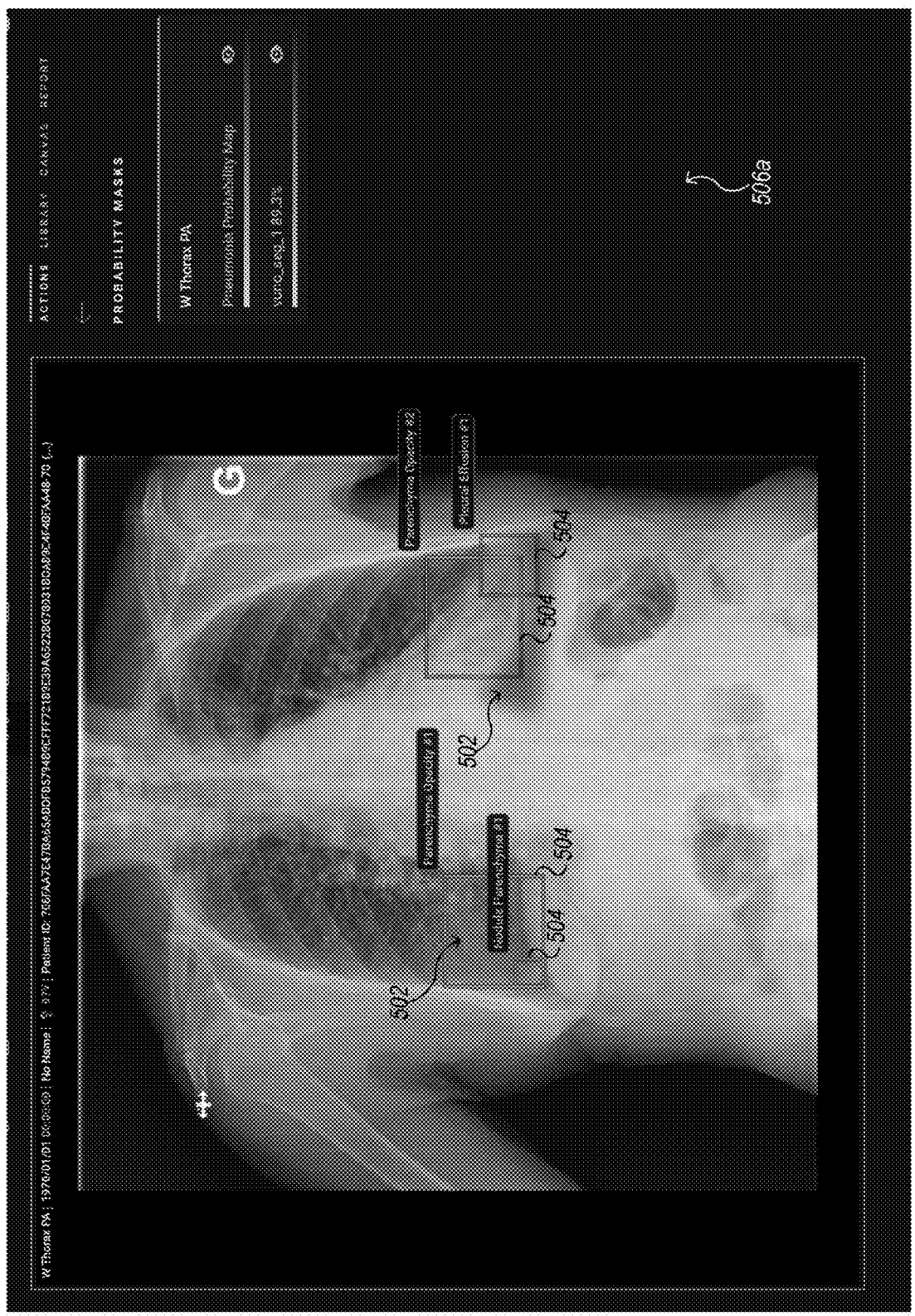
FIGS. 5a and 5b show an example of user interfaces related to medical image analysis based on combining complementary models, in accordance with at least some embodiments of the techniques described herein.
Figure 5B:
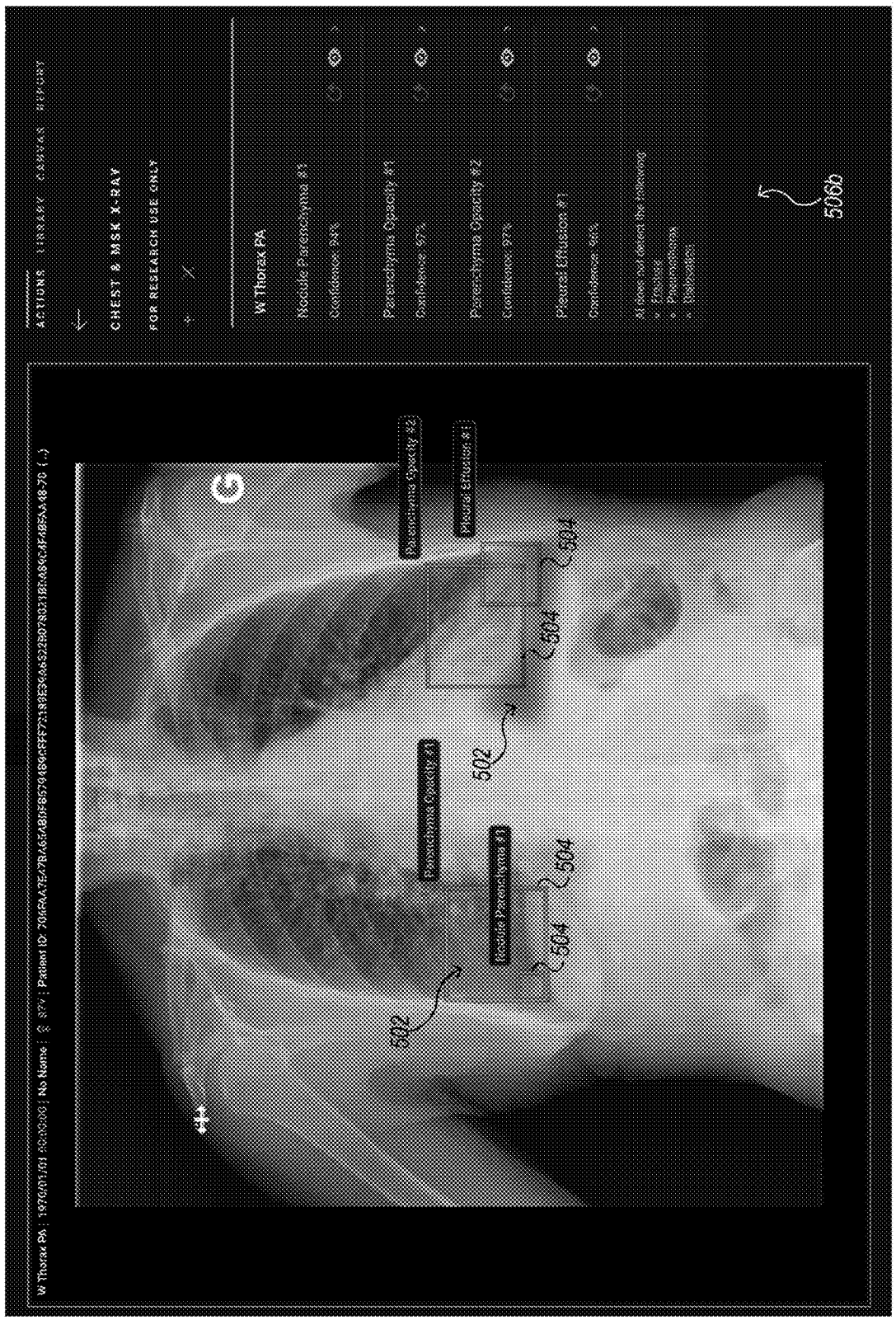

FIGS. 5a and 5b show an example of user interfaces related to medical image analysis based on combining complementary models, in accordance with at least some embodiments of the techniques described herein. As described above, the user interfaces can enable combinations of complementary models to generate AI-enhanced layer(s) atop or beside image data. The user interfaces can present bounding boxes 504 for object detection and localization, graded heat maps 502 corresponding to clinical metrics, or other image overlay enhancements that are generated based on the complementary model results. Additionally, clinically relevant metrics and statistics 506a, 506b can be presented on the side, top, or bottom of the medical image. The user can toggle these overlay enhancements and analyses on or off.

In the example shown in FIGS. 5a and 5b, multiple complementary models are combined for detecting concurrent lesions on a Chest X-ray study. Illustratively, three AI models from Milvue, Vuno and AiDA are applied to medical image data of the Chest X-ray study. Vuno, Milvue and AiDA models returned findings of pneumonia related opacities, and Milvue and AiDA models found a lung nodule. More specifically in FIG. 5a, results from the Vuno and AiDA models show pneumonia probability maps on a Chest X-ray, and in FIG. 5b, results from the Milvue model include a detected lung nodule in addition to the opacities.

Figure 6A:
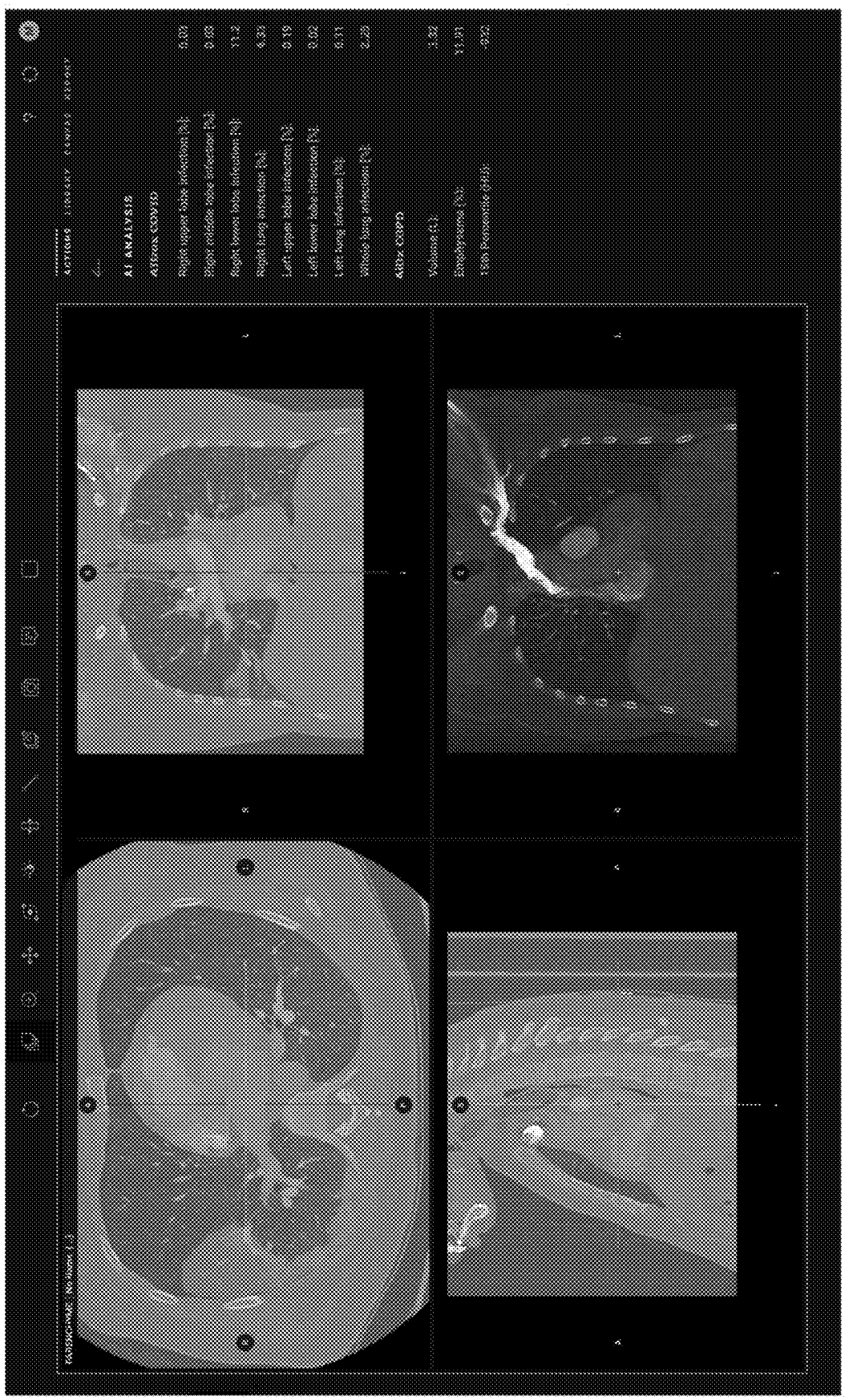
FIGS. 6a and 6b show another example of user interfaces related to medical image analysis based on combining complementary models, in accordance with at least some embodiments of the techniques described herein.
Figure 6B:
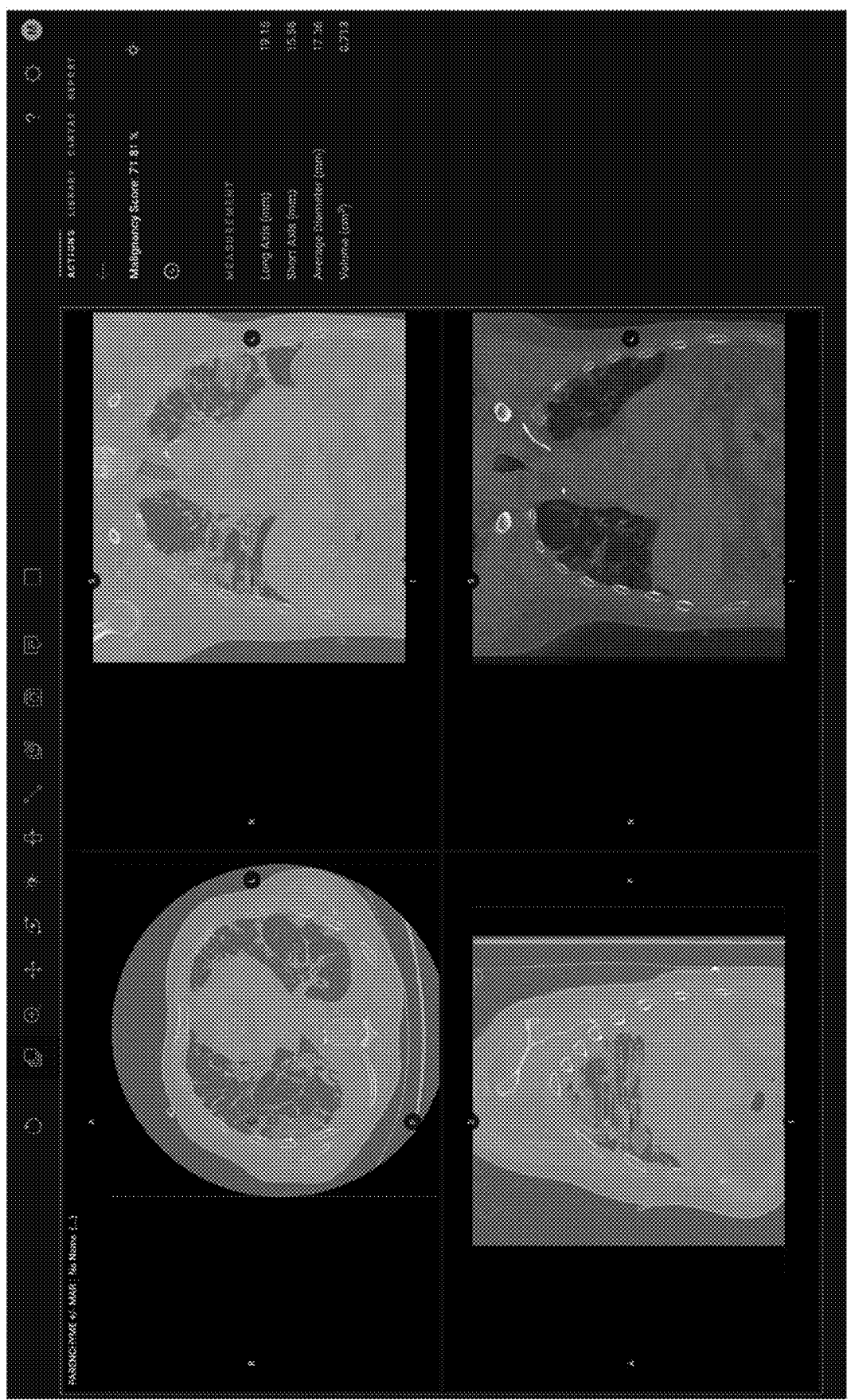

FIGS. 6a and 6b show another example of user interfaces related to medical image analysis based on combining complementary models, in accordance with at least some embodiments of the techniques described herein. The user interfaces facilitate running multiple AI models on Chest CT studies and thereby enable a user (e.g., a radiologist) to look for multiple findings on a CT scan. As shown in FIG. 6a, the Altrox model is utilized to segment COVID opacities and quantify the ratio of the pneumonia burden, while the AiDx COPD model is utilized to evaluate emphysema and air trapping on the same medical imaging data. As shown in FIG. 6b, the Arterys Lung Malignancy Score model is utilized to detect, segment, and provide the likelihood of malignancy on the same medical imaging data.

Figure 7A:
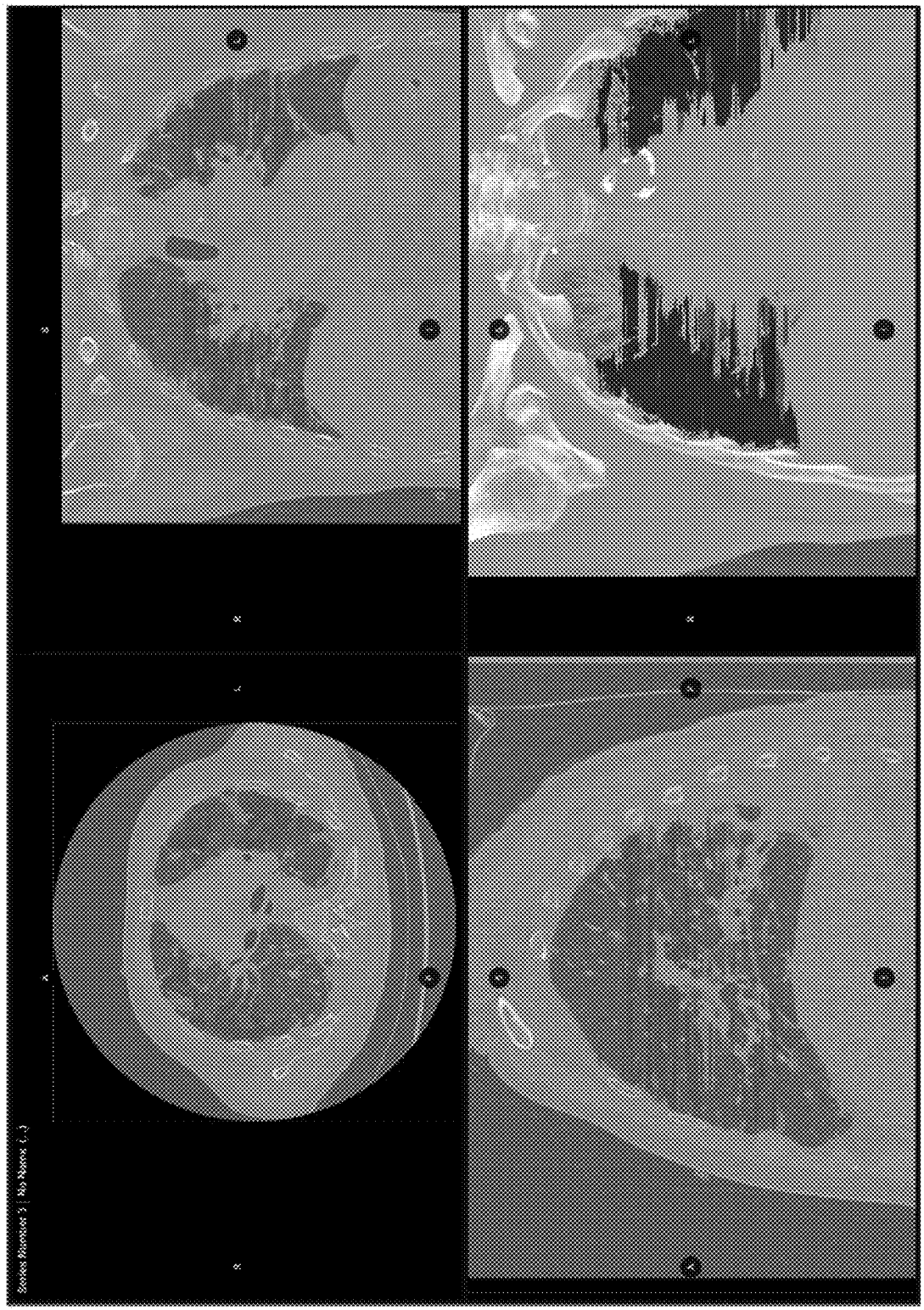
FIGS. 7a and 7b show an example of user interfaces related to medical image analysis based on combining models of the same or similar type, in accordance with at least some embodiments of the techniques described herein.
Figure 7B:
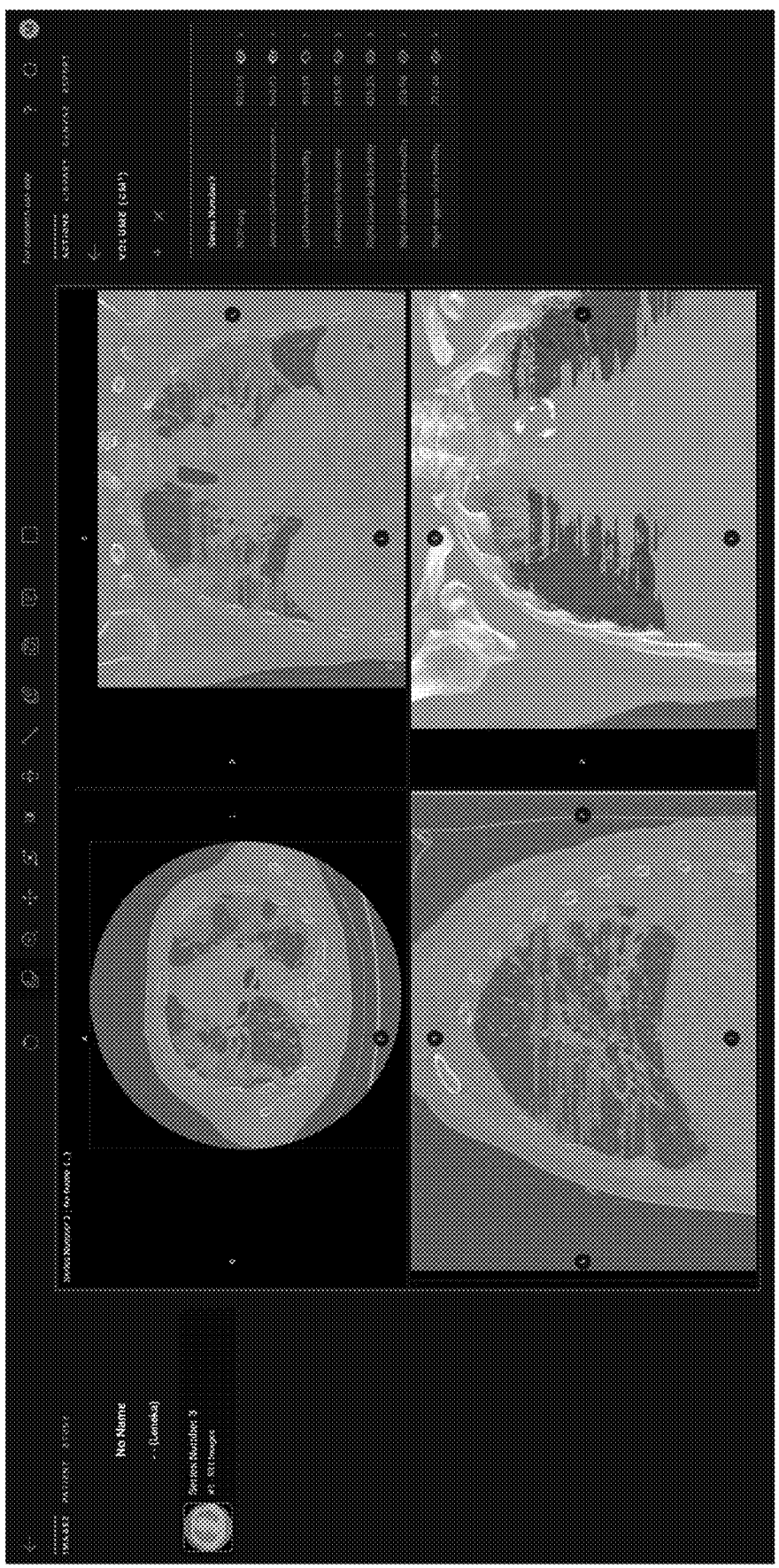

FIGS. 7a and 7b show an example of user interfaces related to medical image analysis based on combining models of the same or similar type, in accordance with at least some embodiments of the techniques described herein. As shown in FIG. 7a, two COVID segmentation models (e.g., Ping AN and Altrox models) are applied on the same Chest CT imaging, and they generate respective COVID lesion masks (shown in two different shades of color) that are concurrently overlaid onto the underlying medical image. This allows a user to get different reads on the estimation of findings, and serves as a basis for the clinical validation of the AI models. Alternatively or in addition, the user interfaces related to combining models of the same or similar type facilitate the quality control process of AI findings, and enable combining results to improve the confidence in the AI findings. As shown in FIG. 7b, the COVID lesion masks generated from the two models are combined (e.g., by a union operation) to show a unified mask in the same shade of color. In various embodiments, the findings generated by different models can be combined in different ways and presented to the user. For example, intersection, union, averaging, weighted averaging, probabilistic sampling, combination of the same or the like can be applied to the findings.

Figure 8A:
FIGS. 8a and 8b show another example of user interfaces related to medical image analysis based on combining models of the same or similar type, in accordance with at least some embodiments of the techniques described herein.
Figure 8B:
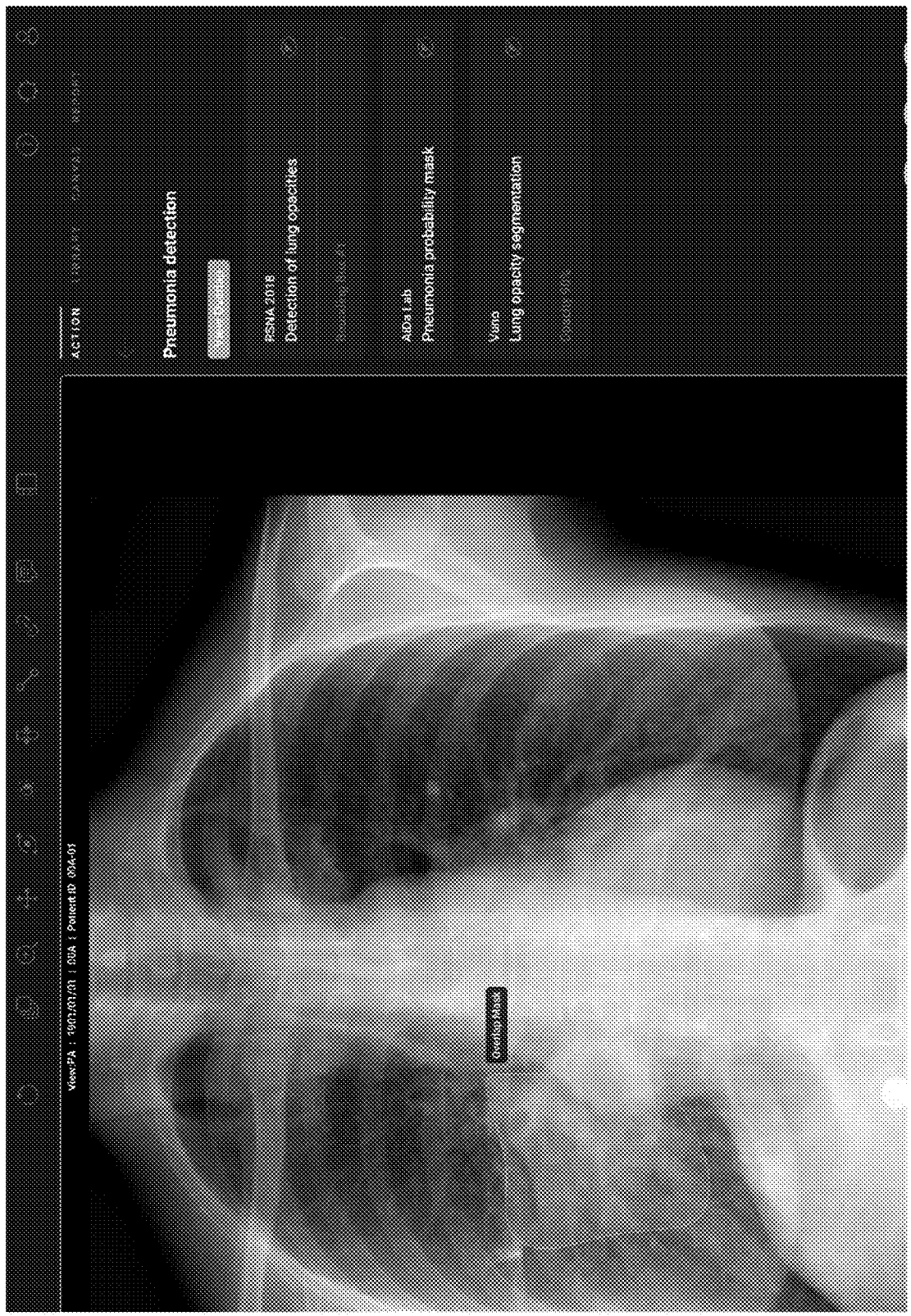

FIGS. 8a and 8b show another example of user interfaces related to medical image analysis based on combining models of the same or similar type, in accordance with at least some embodiments of the techniques described herein. As shown in FIG. 8a, three pneumonia detection models (e.g., Vuno, AiDx, and RSNA2018) are applied on the same Chest X-ray imaging, and they generate respective suspected areas of pneumonia (shown as a segmentation mask, a probability mask, and a bounding box) that are concurrently overlaid onto the underlying medical image. As shown in FIG. 8b, the findings from the three models are combined (e.g., by determining an overlapping area among the three results) to show a unified, overlap mask overlaid onto the underlying medical image.

Figure 9:
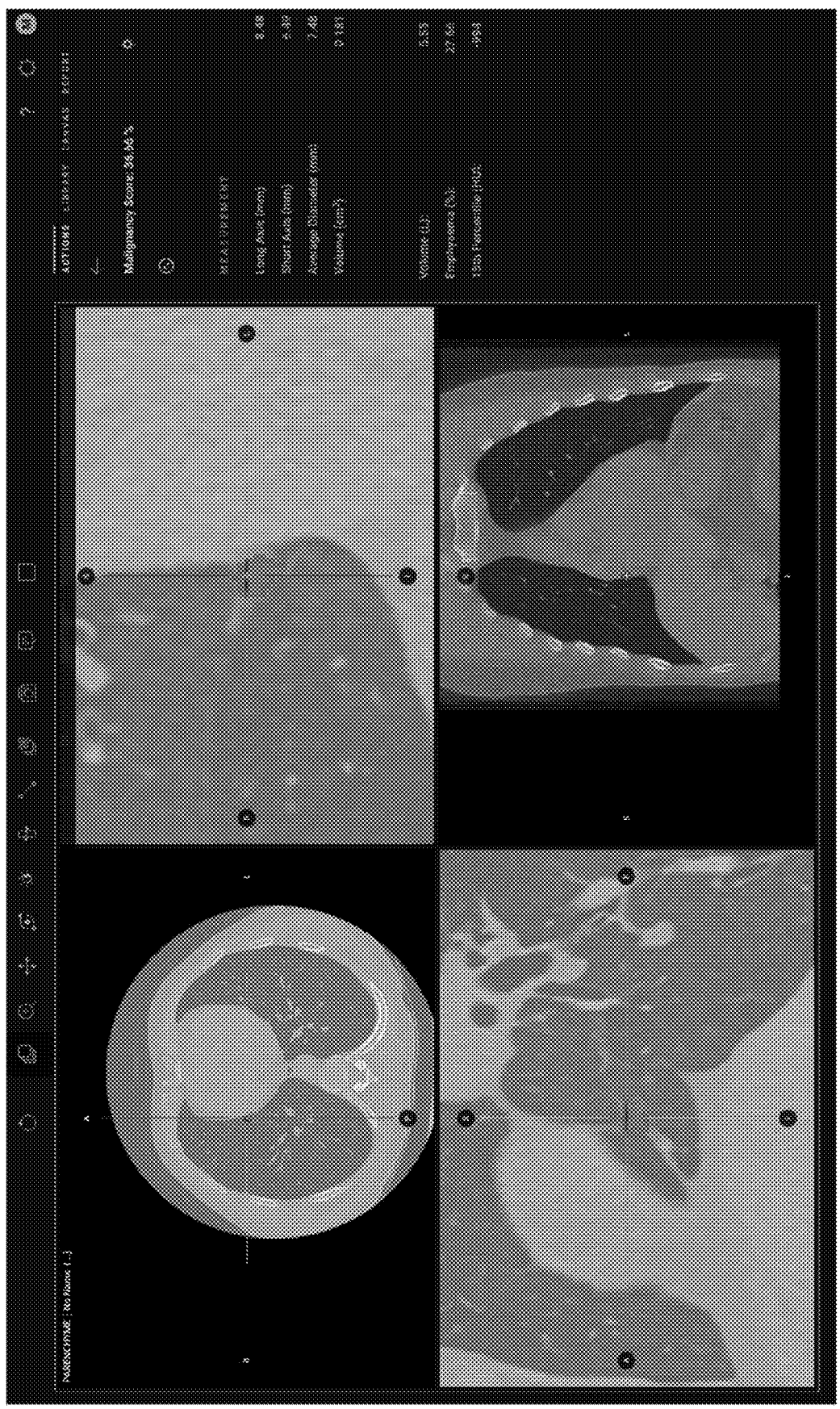
FIG. 9 shows an example of user interfaces related to a configurable workflow for medical image analysis that enables individual models be linked together, in accordance with at least some embodiments of the techniques described herein.

FIG. 9 shows an example of user interfaces related to a configurable workflow for medical image analysis that enables individual models be linked together, in accordance with at least some embodiments of the techniques described herein. As discussed above, using such user interfaces, a user can, within the same view of the medical image(s), search for various models to apply to the image. The search can be done with text input, by viewing popular models, or with other automatically applied filters that take into account the type of image(s) being viewed. The user interfaces enable the user to integrate the selected models into the workflow, which can be a chain, a tree, a lattice, or other hierarchies to collectively produce and render medical imaging analysis results based on the current images. As shown in FIG. 9, a sequence of 4 AI models are used to read images in a Chest CT study for purposes of identifying pathologies: a nodule detection model, a nodule 3D segmentation model, a classification model providing the likelihood of nodule malignancy, and a lobe segmentation model providing the estimation of emphysema and air trapped in the lungs.

Figure 4:
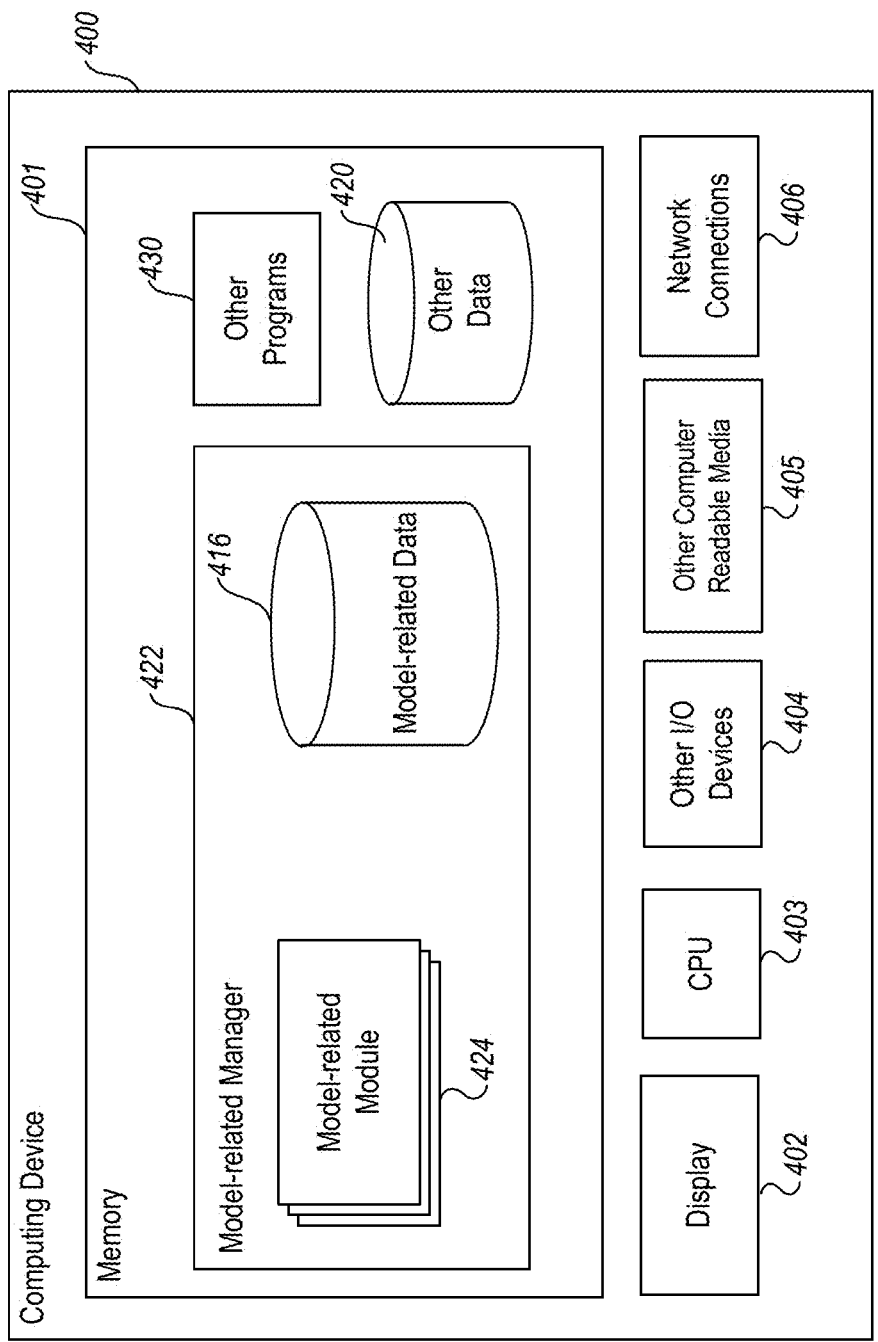
FIG. 4 is a block diagram illustrating elements of an example computing device utilized in accordance with at least some embodiments of the techniques described herein.

FIG. 4 is a block diagram illustrating elements of an example computing device 400 utilized in accordance with at least some embodiments of the techniques described herein. Illustratively, the computing device 400 corresponds to a model platform 118, model provider 128, user device 138, or at least a part thereof.

In some embodiments, one or more general purpose or special purpose computing systems or devices may be used to implement the computing device 400. In addition, in some embodiments, the computing device 400 may comprise one or more distinct computing systems or devices, and may span distributed locations. Furthermore, each block shown in FIG. 4 may represent one or more such blocks as appropriate to a specific embodiment or may be combined with other blocks. Also, the model-related manager 422 may be implemented in software, hardware, firmware, or in some combination to achieve the capabilities described herein.

As shown, the computing device 400 comprises a non-transitory computer memory ("memory") 401, a display 402 (including, but not limited to a light emitting diode (LED) panel, cathode ray tube (CRT) display, liquid crystal display (LCD), touch screen display, projector, etc.), one or more Central Processing Units ("CPU") or other processors 403, Input/Output ("I/O") devices 404 (e.g., keyboard, mouse, RF or infrared receiver, universal serial bus (USB) ports, High-Definition Multimedia Interface (HDMI) ports, other communication ports, and the like), other computer-readable media 405, and network connections 406. The model-related manager 422 is shown residing in memory 401. In other embodiments, some portion of the contents and some, or all, of the components of the model-related manager 422 may be stored on or transmitted over the other computer-readable media 405. The components of the computing device 400 and model-related manager 422 can execute on one or more CPUs 403 and implement applicable functions described herein. In some embodiments, the model-related manager 422 may operate as, be part of, or work in conjunction or cooperation with other software applications stored in memory 401 or on various other computing devices. In some embodiments, the model-related manager 422 also facilitates communication with peripheral devices via the I/O devices 404, or with another device or system via the network connections 406.

The one or more model-related modules 424 is configured to perform actions related, directly or indirectly, to AI or other computational model(s). In some embodiments, the model-related module(s) 424 stores, retrieves, or otherwise accesses at least some model-related data on some portion of the model-related data storage 416 or other data storage internal or external to the computing device 400.

Other code or programs 430 (e.g., further data processing modules, a program guide manager module, a Web server, and the like), and potentially other data repositories, such as data repository 420 for storing other data, may also reside in the memory 401, and can execute on one or more CPUs 403. Of note, one or more of the components in FIG. 4 may or may not be present in any specific implementation. For example, some embodiments may not provide other computer readable media 405 or a display 402.

In some embodiments, the computing device 400 and model-related manager 422 include API(s) that provides programmatic access to add, remove, or change one or more functions of the computing device 400. In some embodiments, components/modules of the computing device 400 and model-related manager 422 are implemented using standard programming techniques. For example, the model-related manager 222 may be implemented as an executable running on the CPU 403, along with one or more static or dynamic libraries. In other embodiments, the computing device 400 and model-related manager 422 may be implemented as instructions processed by a virtual machine that executes as one of the other programs 430. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

In a software or firmware implementation, instructions stored in a memory configure, when executed, one or more processors of the computing device 400 to perform the functions of the model-related manager 422. In some embodiments, instructions cause the CPU 403 or some other processor, such as an I/O controller/processor, to perform at least some functions described herein.

The embodiments described above may also use well-known or other synchronous or asynchronous client-server computing techniques. However, the various components may be implemented using more monolithic programming techniques as well, for example, as an executable running on a single CPU computer system, or alternatively decomposed using a variety of structuring techniques known in the art, including but not limited to, multiprogramming, multi-threading, client-server, or peer-to-peer, running on one or more computer systems each having one or more CPUs or other processors. Some embodiments may execute concurrently and asynchronously, and communicate using message passing techniques. Equivalent synchronous embodiments are also supported by a model-related manager 422 implementation. Also, other functions could be implemented or performed by each component/module, and in different orders, and by different components/modules, yet still achieve the functions of the computing device 400 and model-related manager 422.

In addition, programming interfaces to the data stored as part of the computing device 400 and model-related manager 422, can be available by standard mechanisms such as through C, C++, C#, and Java APIs; libraries for accessing files, databases, or other data repositories; scripting languages such as XML; or Web servers, FTP servers, NFS file servers, or other types of servers providing access to stored data. The model-related data storage 416 and data repository 420 may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules in different ways, yet still achieve the functions of the model-related manager 422.

Furthermore, in some embodiments, some or all of the components of the computing device 400 and model-related manager 422 may be implemented or provided in other manners, such as at least partially in firmware or hardware, including, but not limited to one or more application-specific integrated circuits ("ASICs"), standard integrated circuits, controllers (e.g., by executing appropriate instructions, and including microcontrollers or embedded controllers), field-programmable gate arrays ("FPGAs"), complex programmable logic devices ("CPLDs"), and the like. Some or all of the system components or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium or one or more associated computing systems or devices to execute or otherwise use, or provide the contents to perform, at least some of the described techniques.

The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. In cases where the present patent application conflicts with an application or other document incorporated herein by reference, the present application controls. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A computer-implemented method for facilitating medical image analysis, comprising:
    obtaining a plurality of artificial intelligence (AI) models for medical image analysis from one or more model providers;
    organizing the plurality of models into groups to form associations among the models, wherein at least a subset of the groups reference one another to associate models with one another;
    in response to a user request received from a user device, providing one or more base models selected from the plurality of models;
    searching, based on the one or more base models, the organized plurality of models in accordance with the models' associations to identify one or more additional models as candidates for combining with the one or more base models;
    providing the one or more additional models selected from the organized plurality of models to combine with the one or more base models; and
    causing presentation of medical image analysis results based, at least in part, on applying a combination of the one or more base models and the one or more additional models to target medical image data, wherein causing presentation of the medical image analysis results comprises causing presentation of image overlay features concurrently with one or more images of the target medical image data.

2. The method of claim 1, wherein organizing the plurality of models comprises organizing the plurality of models into a hierarchy of the groups based on grouping criteria.

3. The method of claim 2, wherein the grouping criteria includes at least one of a similarity of input between models, a similarity of output between models, or an overlap between a model's output and another model's input.

4. The method of claim 1, wherein the user request indicates at least one of an analysis purpose, context, applicable medical data, model structure, model input or output, or performance requirement.

5. The method of claim 1, further comprising selecting the one or more base models based, at least in part, on the associations among the models.

6. The method of claim 1, wherein the one or more additional models and the one or more base models are designed to receive same or overlapping input features and to generate different output features.

7. The method of claim 1, wherein the one or more additional models and the one or more base models are designed to generate same or overlapping output features.

8. The method of claim 1, wherein the one or more additional models and the one or more base models are linkable to form a configurable workflow.

9. The method of claim 8, wherein the configurable workflow includes at least one of a chain, tree, or lattice structure to link models.

10. The method of claim 1, wherein causing presentation of the medical image analysis results comprises causing presentation of one or more user interfaces via the user device.

11. The method of claim 10, wherein causing presentation of the medical image analysis results further comprises causing presentation of image overlay features corresponding to results from the combination of the one or more base models and the one or more additional models, via the one or more user interfaces.

12. One or more non-transitory computer-readable media collectively storing contents that, when executed by one or more processors, cause the one or more processors to perform actions comprising:
   organizing a plurality of models for medical image analysis into groups to form associations among the models, wherein at least a subset of the groups reference one another to associate models with one another;
   searching, based on one or more first models, the organized plurality of models in accordance with the models' associations to identify one or more second models for combining with the one or more first models;
   combining at least a subset of the one or more first models with at least a subset of the one or more second models to form a combination of models based, at least in part, on a user request; and
   causing presentation of medical image analysis results based, at least in part, on applying the combination of models to target medical image data, wherein causing presentation of the medical image analysis results comprises causing presentation of image overlay features concurrently with one or more images of the target medical image data.

13. The one or more non-transitory computer-readable media of claim 12, wherein the image overlay features include at least one of bounding boxes for object detection and localization, or graded heat maps corresponding to clinical metrics.

14. The one or more non-transitory computer-readable media of claim 12, wherein the image overlay features include a single feature that integrates results generated from individual models that form the combination of models.

15. The one or more non-transitory computer-readable media of claim 14, wherein the single feature is generated by at least one of intersection, union, averaging, weighted averaging, or probabilistic sampling operation.

16. A system, comprising:
   one or more processors; and
   non-transitory memory storing contents that, when executed by the one or more processors, cause the system to:
      organize a plurality of models into groups for medical image analysis to form associations among the models, wherein at least a subset of the groups reference one another to associate models with one another;
      search, based on one or more first models, the organized plurality of models in accordance with the models' associations to identify one or more second models for combining with the one or more first models;
      combine at least a subset of the one or more first models with at least a subset of the one or more second models to form a combination of models based, at least in part, on a user request; and
      cause presentation of medical image analysis results based, at least in part, on applying the combination of models to target medical image data, wherein causing presentation of the medical image analysis results comprises causing presentation of image overlay features concurrently with one or more images of the target medical image data.

17. The system of claim 16, wherein organizing the plurality of models comprises organizing the plurality of models into a hierarchy of the groups based on grouping criteria.

18. The system of claim 16, wherein individual models that form the combination of models are designed to receive same or overlapping input features and to generate different output features.

19. The system of claim 16, wherein individual models of that form the combination of models are designed to generate same or overlapping output features.

20. The system of claim 16, wherein individual models of that form the combination of models are linkable to form a workflow including at least one of a chain, tree, or lattice structure to link models.

* * * * *